US005652125A

United States Patent [19]
Scotti et al.

[11] Patent Number: 5,652,125
[45] Date of Patent: Jul. 29, 1997

[54] PROCESS FOR PREPARING DAUNORUBICIN

[75] Inventors: Claudio Scotti, Motta Visconti, Italy; Charles Richard Hutchinson, Cross Plains, Wis.; Anna Luisa Colombo; Silvia Filippini, both of Milan, Italy

[73] Assignee: Pharmacia S.p.A., Milan, Italy

[21] Appl. No.: 660,765

[22] Filed: Jun. 10, 1996

[51] Int. Cl.$^6$ ............... C12P 19/56; C12N 1/19; C12N 15/09; C07H 21/04

[52] U.S. Cl. ............ 435/78; 435/252.35; 435/320.1; 536/23.7

[58] Field of Search ................. 435/69.1, 91.1, 435/183, 252.35, 886, 78; 536/23.7

[56] References Cited

U.S. PATENT DOCUMENTS

5,364,781  11/1994  Hutchinson et al. ............. 435/252.3

OTHER PUBLICATIONS

Ye et al., Isolation and sequence analysis of polyketide synthase genes from the daunomycin–producing Streptomyces spp. strain C5. J. Bacteriol. vol. 176(20):6270–6280 Oct. 31, 1994.

Silvia Filippini, et al.; *Streptomyces peucetius daunorubicin biosynthesis gene, dnrF: sequence and heterologous expression*; Microbiology (1995), 141, 1007–1016.

Ann Grimm, et al.; *Characterization of the Streptomyces peucetius ATCC 29050 genes encoding doxorubicin polyketide synthase*; Gene 151 (1994) 1–10.

Mark A. Gallo, et al.; *The dnrM gene in Streptomyces peucetius contains a naturally occurring frameshift mutation that is suppressed by another locus outside of the daunorubicin–production gene cluster*; Microbiology (1996), 142, 269–275.

Krishnamurthy Madduri, et al.; *Functional Characterization and Transcriptional Analysis of a Gene Cluster Governing Early and Late Steps in Daunorubicin Biosynthesis in Streptomyces peucetius*; Journal of Bacteriology Jul. 1995, 177 pp.. 3879–3884.

Krishnamurthy Madduri, et al.; *Cloning and Sequencing of a Gene Encoding Carminomycin 4–)–Methyltransferase from Streptomyces peucetius and Its Expression in Escherichia coli*; Journal of Bacteriology, Jun. 1993, 175 pp. 3900–3904.

Kim J. Stutzman–Engwall, et al.; *Regulation of Secondary Metabolism in Streptomyces spp. and Overproduction of Daunorubicin in Streptomyces peucetius*; Journal of Bacteriology, Jan. 1992, 174 pp. 144–154.

Krishnamurthy Madduri, et al.; *Functional Characterization and Transcriptional Analysis of the $dnrR_1$ Locus, Which Controls Daunorubicin Biosynthesis in Streptomyces peucetius*; Journal of Bacteriology, Mar. 1995, 177 pp. 1208–1215.

Sharee L. Otten, et al.; *Regulation of Daunorubicin Production in Streptomyces peucetius by the $dnrR_2$ Locus*; Journal of Bacteriology, Mar. 1995, 177 pp. 1216–1224.

Michael L. Dickens, et al.; *Cloning, Sequencing, and Analysis of Aklaviketone Reductase from Streptomyces sp. Strain C5*; Journal of Bacteriology, Jun. 1996, 178 pp. 3384–3388.

Sharee L. Otten, et al.; *Cloning and Characterization of the Streptomyces peucetius dnrQS Genes Ecoding a Daunosamine Biosynthesis Enzyme and a Glycosyl Transferase Involved in Daunoribicin Biosynthesis*; Journal of Bacteriology, No. 1995, 177 pp. 6688–6692.

*Primary Examiner*—David Guzo
*Assistant Examiner*—William Sandals
*Attorney, Agent, or Firm*—Nikaido Marmelstein Murray & Oarm LLP

[57] ABSTRACT

The ability to improve the conversion of ε-rhodomycinone to daunorubicin can be conferred on a bacterial host transformed with a recombinant vector comprising a DNA coding for an appropriate protein useful for that conversion. Furthermore, the bacterial host may have a mutation that blocks the function of a gene of daunorubicin metabolism.

17 Claims, 3 Drawing Sheets

PROCESS FOR PREPARING DAUNORUBICIN

FIELD OF THE INVENTION

The present invention concerns a process for improving the production of daunorubicin by conversion of ε-rhodomycinone to daunorubicin by means of a recombinant strain bearing a deletion in a gene of daunorubicin metabolism and transformed with the gene coding for another enzyme of daunorubicin biosynthesis.

BACKGROUND OF THE INVENTION

The anthracyclines of the daunorubicin group, such as doxorubicin, carminomycin and aclacinomycin and their synthetic analogs, are among the most widely employed agents in antitumoral therapy [F. Arcamone, *Doxorubicin*, Academic Press, New York, 1981, pp. 12–25; A. Grein, Process Biochem. 16:34 (1981); T. Kaneko, Chimicaoggi May:11 (1988); C. E. Myers et al., "Biochemical mechanisms of tumor cell kill". In: Anthracycline and Anthracenedione-Based Anti-Cancer Agents (Lown, J. W., ed.), Elsevier, Amsterdam, pp. 527–569, 1988; J. W. Lown, Pharmac. Ther. 60:185–214 (1993)].

The anthracyclines of the daunorubicin group are naturally occuring compounds produced by various strains of Streptomyces and *Actinomyces carminata*. Doxorubicin is mainly produced by *S. peucetius* subsp. *caesius* while daunorubicin is produced by *S. peucetius*, as well other Streptomyces, for example *S. peucetius* ATCC 27952 is described in U.S. Pat. No. 3,590,028, *S. peucetius* 29050 in U.S. Pat. No. 4,012,284, as well as the other Streptomyces.

In particular, the doxorubicin and daunorubicin are made by *S. peucetius*, ATCC 29050 and 27952 from malonic acid, propionic acid, and glucose by the pathway summarized in Grein, Advan. Appl. Microbiol. 32:203 (1987) and in Eckardt and Wagner, J. Basic Microbiol. 28:137 (1988). Aklavinone (11-deoxy-ε-rhodomycinone), ε-rhodomycinone and carminomycin are established intermediates in this process. The final step in this pathway in *S. peucetius* 27952 involves the hydroxylation of daunorubicin to doxorubicin [F. Arcamone et al., Biotechnol. Bioeng. 11:1101 (1969)].

Daunorubicin is known to be converted to 4'-O-glycosides called baumycins in Streptomyces species [Y. Takahashi, H. Naganawa, T. Takeuchi, H. Umezawa, T. Komiyama, T. Oki, and T. Inui. J. Antiblot. 30:622 (1977)].

Furthermore, the *S. peucetius* 29050 and 27952 strains usually produce much more ε-rhodomycinone than daunorubicin or doxorubicin. Since the therapeutically valueless ε-rhodomycinone cannot easily be converted to the important antitumor anthracycline drugs by chemical synthesis or biotransformation, it represents a commercially useless by-product of daunorubicin fermentations.

Up to now, several genes for daunorubicin and doxorubicin biosynthesis and resistance have been obtained from *S. peucetius* 29050 and *S. peucetius* 27952 by cloning experiments, but none of them were identified as conferring to their host the ability of converting ε-rhodomycinone into daunorubicin.

SUMMARY OF THE INVENTION

Figure 1:
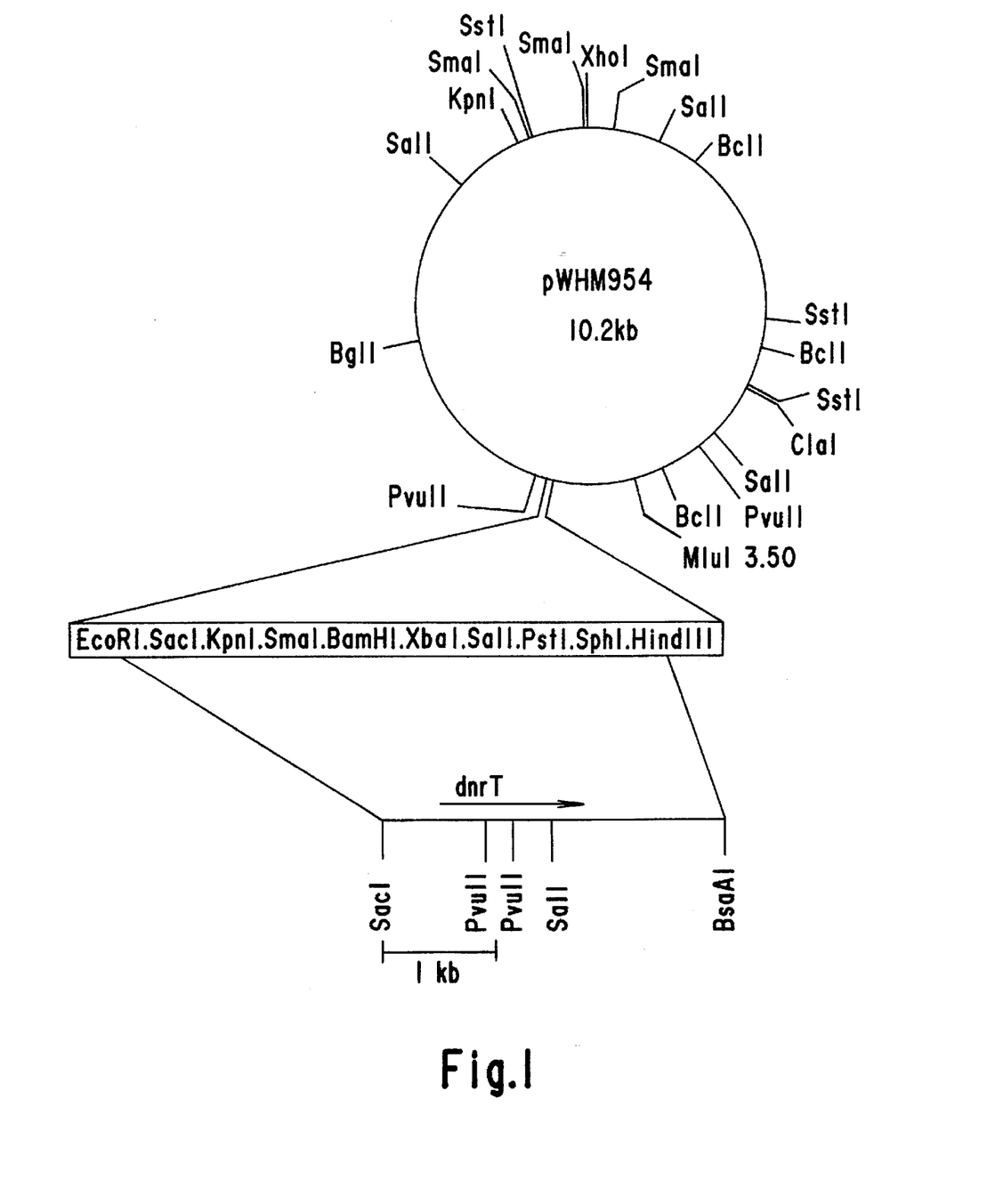

The present invention provides a process for preparing daunorubicin by means of a bacterial host transformed with a recombinant vector comprising a DNA which codes for a protein required for the conversion of ε-rhodomycinone to daunorubicin, preferably having the configuration of restriction sites shown in FIG. 1 or a restriction fragment derived therefrom containing a gene coding for the same or functionally equivalent protein.

Figure 2:
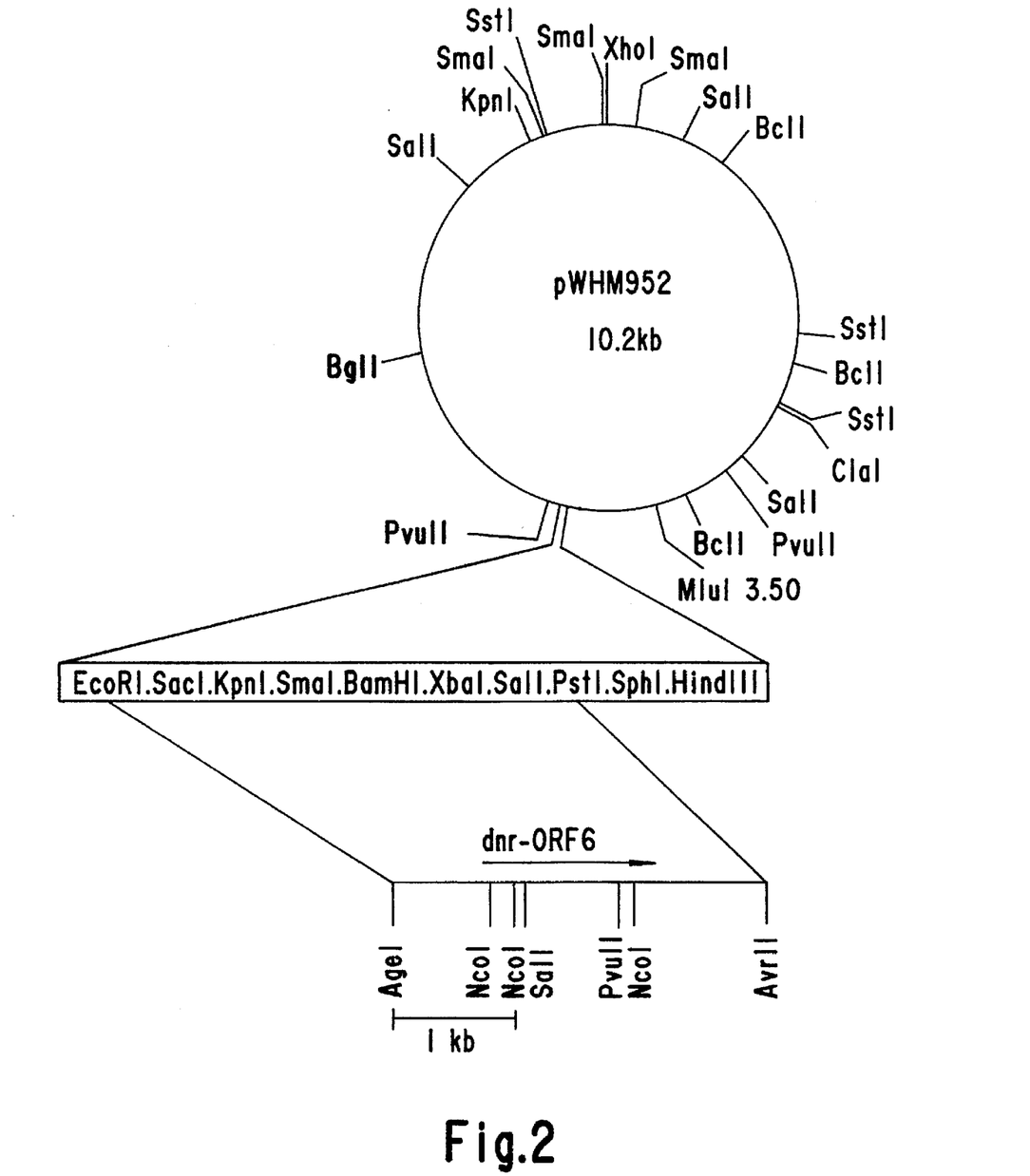

Preferably the bacterial host is a strain of *Streptomyces spp* producing daunorubicin, having a mutation blocking the function of a gene of daunorubicin metabolism. Said blocked gene is preferably comprised in the DNA fragment having the configuration of restriction sites shown in FIG. 2 or in a fragment derived therefrom containing a gene, dnr-ORF6, coding for a protein involved in the metabolism of daunorubicin. The streptomyces host having a mutation in dnr-ORF6 is transformed with a recombinant vector having an insert DNA coding for an ε-rhodomycinone conversion protein, preferably having the configuration of restriction sites shown in FIG. 1 or a restriction fragment derived therefrom containing a gene dnrT coding for said protein.

The invention also provides:

a) DNA segment coding an ε-rhodomycinone conversion protein, preferably that shown in FIG. 1, SEQ ID 1, or a restriction fragment derived therefrom containing a gene dnrT, coding for said protein;

b) recombinant vectors that are able to increase the number of copies of dnrT gene, and the amount of its product in a strain of *Streptomyces spp* that produces daunorubicin;

c) a strain of *S. peucetius*, preferably ATCC 29050, having a mutation blocking the function of the dnr-ORF6 gene into which such recombinant vectors can be introduced by transformation, thereby increasing the conversion of ε-rhodomycinone to daunorubicin.

BRIEF DESCRIPTION OF THE DRAWINGS

FIG. 1 is a restriction map analysis of the DNA of the invention, pWHM954. This is an insert in recombinant plasmid pWHM3, an *Escherichia coli*-Streptomyces shuttle vector [Vara et al., J. Bacteriol. 171:5872 (1989)], that was constructed by insertion of a 2.97 kb SacI-BsaAI DNA fragment containing the dnrT gene or any other fragment of at least 1.52 kb that contains the entire dnrT gene, which was obtained from clones described in Stutzman-Engwall and Hutchinson, Proc. Natl. Acad. Sci. USA 86:3135 (1988) and Otten et al., J. Bacteriol. 172:3427 (1990), into the SacI-HincII sites of the polylinker region of pUC19 [Yanisch-Perron et al., Gene 33:103 (1985)], then moving the gene as an EcoRI-HindIII segment into the polylinker region of pWHM3. The map shown in FIG. 1 does not necessarily provide an exhaustive listing of all restriction sites present in the DNA segment. However, the reported sites are sufficient for an unambiguous recognition of the segments.

SEQ ID NO. 1 is a schematic illustration of a nucleotide sequence of the dnrT DNA segment which corresponds to that encoding a protein required for daunorubicin biosynthesis. This covers most of the region between the EcoRI and the HindIII restriction sites of pWHM954 and shows the coding strand in the 5' to 3' direction. The derived amino acid sequence of the translated open reading frame encoding a protein required for daunorubicin biosynthesis is shown below the nucleotide sequence of the dnrT gene, as SEQ ID NO. 2.

FIG. 2 is the restriction map analysis of the second DNA, pWHM952, whose function is blocked for a further object of the invention. This is an insert in recombinant plasmid pWHM3 that was constructed by insertion of a 2.93 kb AgeI-AvrII DNA fragment, which was obtained from clones described in Stutzman-Engwall and Hutchinson, Proc. Natl. Acad. Sci. USA 86:3135 (1988) and Otten et al., J. Bacteriol. 172:3427 (1990), into the XmaI-XbaI sites of the polylinker region of pUC19, then moving the gene as an EcoRI-PstI segment into the polylinker region of pWHM3. The map shown in FIG. 2 does not necessarily provide an exhaustive listing of all restriction sites present in the DNA segment. However, the reported sites are sufficient for an unambiguous recognition of the segments.

SEQ ID NO. 3 is a schematic illustration of a nucleotide sequence of the dnr-ORF6 DNA segment which corresponds to that encoding a protein required for daunorubicin metabolism. This covers most of the region between the EcoRI and the PstI restriction sites of pWHM952 and shows the coding strand in the 5' to 3' direction. The derived amino acid sequence of the translated open reading frame encoding a protein required for daunorubicin metabolism is shown below the nucleotide sequence of the dnr-ORF6 gene, as SEQ ID NO. 4.

FIG. 3 is a restriction map for the dnr-ORF6 and dnrT genes region. The location and the direction of transcription of the two genes are indicated by arrows. The fragments used for the construction of plasmids pWHM962, pWHM959, pWHM954 and pWHM952 are shown in the lower portion. Restriction site abbreviations: Ac, AccI; Ag, AgeI; Al, AlwNI; Av, AvrII; Ba, BamHI; Bs, BsaAI; Na, NarI; Sa, SacI; Sp, SphI.

DETAILED DESCRIPTION OF THE INVENTION

The present invention provides an isolated DNA molecule encoding an ε-rhodomycinone conversion protein.

The DNA molecule typically consists essentially of the sequence of SEQ ID NO: 1, which sequence will be referred to as the "dnrT" sequence. The deduced amino acid sequence of the ε-rhodomycinone conversion protein encoded by SEQ ID No:1 is shown in SEQ ID No: 2.

The DNA molecule of the invention may comprise all or part of the 2.97 kb SacI-BsaAI fragment of FIG. 1.

When the DNA molecule of the invention comprises only part of the 2.97 kb SacI-BsaAI fragment, the part must function as an ε-rhodomycinone conversion protein. The part is typically at least 1.52 kb in length.

The invention includes a DNA molecule which encodes an ε-rhodomycinone conversion protein having a sequence at least 75% identical to the sequence of SEQ ID No: 2. The sequence may be at least 80%, at least 90%, at least 95%, at least 98% or at least 99% identical to the sequence of SEQ ID No: 2.

The sequence of SEQ ID No: 2 may be modified by substitution, deletion, insertion, extension, functionalisation or chemical modification. A substitution, deletion, insertion or extension may involve one or more amino acids, for example one, two, three, four, five, eight, fifteen or twenty amino acids. In general, the physicochemical nature of SEQ ID No: 2 should be preserved in a modified sequence. The modified sequence should generally be similar in charge, hydrophobicity/hydrophilicity and size. Candidate substitutions are those which lead to an amino acid from one of the following groups being substituted by a different amino acid from the same group:

H, R and K

I, L, V and M

A, G, S and T

D, E, P and N.

DNA molecules encoding the modified sequences may be made using conventional techniques. For example, they may be made using conventional DNA synthesis, site-directed mutagenesis and recombinant DNA techniques. Suitable techniques are described in Sambrook et al (1989) Molecular Cloning: A Laboratory Manual, 2nd Ed., Cold Spring Harbor Laboratory, Cold Spring Harbor, N.Y.

For dnrT to be expressed, the DNA may carry its own transcriptional control sequence and, in particular, its own promoter which is operably connected to the gene and which is recognised by a host cell RNA polymerase. Alternatively, the insert DNA or restriction fragment may be ligated to another transcriptional control sequence in the correct fashion or cloned into a vector at a restriction site appropriately located neighboring a transcriptional control sequence in the vector.

An insert DNA or restriction fragment carrying a dnrT gene may be cloned into a recombinant DNA cloning vector. Any autonomously replicating and/or integrating agent comprising a DNA molecule to which one or more additional DNA segments can be added may be used. Typically, however, the vector is a plasmid. A preferred plasmid is the high copy number plasmid pWHM3 or pIJ702 [Katz et al., J. Gen. Microbiol. 129:2703 (1983)]. Other suitable plasmids are pIJ385 [Mayeri et al., J. Bacteriol. 172:6061 (1990)], pIJ680 (Hopwood et al., *Genetic Manipulation of Streptomyces. A Laboratory Manual*, John Innes Foundation, Norwich, UK, 1985), pWHM601 [Guilfoile and Hutchinson, Proc. Natl. Acad. Sci. USA 88:8553 (991)] or pSET152 [Bierman et al., Gene 116:43–49 (1992)]. Any suitable technique may be used to insert the insert DNA or restriction fragment thereof into the vector. Insertion can be achieved by ligating the DNA into a linearized vector at an appropriate restriction site. For this, direct combination of sticky or blunt ends, homopolymer tailing, or the use of a linker or adapter molecule may be employed.

The recombinant vector is used to transform a suitable host cell. The host cells may be ones that are daunorubicin- or doxorubicin-sensitive, i.e., cannot grow in the presence of a certain amount of daunorubicin or doxorubicin, or that are daunorubicin- or doxorubicin-resistant. The host may be a microorganism. Strains of *S. peucetius* that do not or do produce anthracyclines, respectively, may therefore be transformed. The S. peucetius dnr-ORF6 mutant strain (ATCC 55761, date of deposit Apr. 16, 1996) represents a particularly suitable host. It was obtained by introduction of the internal 0.411-kb BsaA1 segment of the dnr-ORF6 gene, cloned on a temperature-sensitive plasmid such as pKC1139 (M. Bierman et al., Gene 116:43–49), into the 29050 strain and subsequent isolation of apramycin resistant transformants in which the recombinant plasmid has recombined with the dnr-ORF6 gene and inactivated it (see also Example 1). Transformants of Streptomyces strains are typically obtained by protoplast transformation.

The conversion process can be carried out either by using directly the free or immobilized transformed cells.

The recombinant vectors of the present invention may also be used to transform a suitable host cell, which produces daunorubicin, in order to enhance the bioconversion of ε-rhodomycinone to daunorubicin.

The host cells may be ones that are daunorubicin- or doxorubicin-resistant, i.e., can grow in the presence of any amount of daunorubicin or doxorubicin. Strains of *S. peucetius*, in particular *S. peucetius* 29050 and other strains of *Streptomyces spp* that produce anthracyclines may therefore be transformed. Transformants of Streptomyces strains are typically obtained by protoplast transformation.

The invention includes a process for producing daunorubicin, which process comprises (i) culturing a host cell of the invention,
(ii) transforming the said host with a vector of the invention, and
(iii) isolating the daunorubicin from the culture;

In this process the host cell may be cultured at from 20° to 40° C., for example from 30° to 37° C.

The culture is preferably carried out with agitation.

The insert DNAs are obtained from the genomic DNA of S. peucetius 29050. This strain has been deposited at the American Type Culture Collection, Rockville, Md., USA under the accession number ATCC 29050. A strain derived from *S. peucetius* 29050, like *S. peucetius* 27952, may also be used, which typically is also able to convert ε-rhodomycinone to daunorubicin. Insert DNAs may therefore be obtained by:

(a) preparing a library of the genomic DNA of *S. peucetius* 29050 or a strain derived therefrom;

(b) screening the library for clones with the ability to convert ε-rhodomycinone to daunorubicin in the *S. peucetius* dnrT mutant; and (c) obtaining an insert DNA from a recombinant vector that forms part of the library and that has been screened as positive for the ability to convert ε-rhodomycinone to daunorubicin in the *S. peucetius* dnrT mutant. The dnrT mutant strain (ATCC 55762, date of deposit Apr. 16, 1996) is obtained by insertional inactivation of the dnrT gene present in *S. peucetius* 29050 in a way analogous to that described above for the inactivation of the dnr-ORF6 gene, as explained in Example 2.

To obtain the dnrT gene, the library may be prepared in step (a) by partially digesting the genomic DNA of *S. peucetius* 29050 or a strain derived therefrom; or by screening a library of S. peucetius genomic DNA that has been enriched for, or specifically contains, the cluster of daunorubicin biosynthesis genes. The restriction enzyme MboI is preferably used for genomic DNA, but for the library containing the cluster of daunorubicin biosynthesis genes, the restriction enzymes SacI or BsaAI are preferred. The DNA fragments thus obtained can be size fractionated; fragments from 3 to 5 kb in size are preferred for genomic DNA and 2.1 kb SacI or 1.3 to 3.3 kb BsaAI for DNA fragments from the library containing the cluster of daunorubicin biosynthesis genes. These fragments are ligated into a linearized vector such as pWHM3, pIJ702 or pKC505 [M. A. Richardson et al., Gene 61:231 (1987)]. Host cells are transformed with the ligation mixture. Typically, the host cells cannot produce daunorubicin and can be daunorubicin- and doxorubicin-sensitive; for example, sensitive to 10 microgram or less of daunorubicin or doxorubicin per ml. For example, *S. peucetius* dnrT mutant protoplasts [Stutzman-Engwall and Hutchinson, Proc. Natl. Acad. Sci. USA 86:3135 (1988) and Otten et al., J. Bacteriol. 172:3427 (1990)] may be transformed.

In step (b), the transformants thus obtained are screened for the ability to convert the accumulated ε-rhodomycinone to daunorubicin and excrete daunorubicin. Clones able to convert ε-rhodomycinone to daunorubicin are identified by chromatographic analysis of extracts of a culture medium containing ε-rhodomycinone for the presence of daunorubicin. Such clones are isolated and recombinant vectors contained therein are extracted. On digestion of the recombinant vectors with suitable restriction enzymes in step (c), the *S. peucetius* 29050 DNA inserted into each vector may be identified, sized and mapped. In this way, it may be checked that the vector contains an insert DNA of the invention.

Further, two or more overlapping inserts may be isolated that are wholly or partly embraced within the DNA of the invention. These may be fused together by cleavage at a common restriction site and subsequent ligation to obtain a DNA of the invention, and pared in length using appropriate restriction enzymes if necessary. Restriction fragments of an insert DNA that contains the dnrT gene may be obtained in step (c) also by cleaving an insert DNA with an appropriate restriction enzyme. The following examples illustrate the invention.

Materials and Methods

Bacterial Strains and Plasmids

E. coli strains DH5α or JM109, which are sensitive to ampicillin and apramycin, are used for subcloning DNA fragments. S. peucetius dnr-ORF6 mutant that does not produce daunorubicin glycosides is used for expression of the dnr-ORF6 or dnrT genes. The plasmid cloning vectors are pUC18/19 [(Yanisch-Perron et al., Gene 33:103 (1985)] and pWHM3 [Vara et al., J. Bacteriol. 171:5872 (1989)].

Media and Buffers

E. coli DH5a and JM109 are maintained on LB agar (Sambrook et al., *Molecular Cloning. A Laboratory Manual*, 2nd ed. Cold Spring Harbor Press, Cold Spring Harbor, N.Y., 1989). When selecting for transformants, ampicillin or apramycin are added at concentrations of 100 microgram/ml and 50 microgram/ml, respectively. S. peucetius dnr-ORF6 is maintained on ISP4 agar (Difco Laboratories, Detroit, Mich.) for the preparation of spores and on R2YE agar (Hopwood et al., *Genetic Manipulation of Streptomyces. A Laboratory Manual*, John Innes Foundation, Norwich, UK, 1985) for the regeneration of protoplasts.

Subcloning DNA Fragments

DNA samples are digested with appropriate restriction enzymes and separated on agarose gels by standard methods (Sambrook et al., *Molecular Cloning. A Laboratory Manual*, 2nd ed. Cold Spring Harbor Press, Cold Spring Harbor, N.Y., 1989). Agarose slices containing DNA fragments of interest are excised from a gel and the DNA is isolated from these slices using the GENECLEAN device (Bio101, La Jolla, Calif.) or an equivalent. The isolated DNA fragments are subcloned using standard techniques (Sambrook et al., *Molecular Cloning. A Laboratory Manual*, 2nd ed. Cold Spring Harbor Press, Cold Spring Harbor, N.Y., 1989) into E. coli for routine manipulations, including DNA sequencing, and E. coli/Streptomyces shuttle vectors or Streptomyces vectors for expression and biotransformation experiments.

Transformation of Streptomyces Species and E. coli

Competent cells of E. coli are prepared by the calcium chloride method (Sambrook et al., *Molecular Cloning. A Laboratory Manual*, 2nd ed. Cold Spring Harbor Press, Cold Spring Harbor, N.Y., 1989) and transformed by standard techniques (Sambrook et al., *Molecular Cloning. A Laboratory Manual*, 2nd ed. Cold Spring Harbor Press, Cold Spring Harbor, N.Y., 1989). S. peucetius dnr-ORF6 mycelium is grown in R2YE medium (Hopwood et al., *Genetic Manipulation of Streptomyces. A Laboratory Manual*, John Innes Foundation, Norwich, UK, 1985) and harvested after 48 hr. The mycelial pellet is washed twice with 10.3% (wgt/vol) sucrose solution and used to prepare protoplasts according to the method outlined in the Hopwood manual (Hopwood et al., *Genetic Manipulation of Streptomyces. A Laboratory Manual*, John Innes Foundation, Norwich, UK, 1985). The protoplast pellet is suspended in about 300 microlitres of P buffer (Hopwood et al., *Genetic Manipulation of Streptomyces. A Laboratory Manual*, John Innes Foundation, Norwich, UK, 1985) and a 50 microlitre aliquot of this suspension is used for each transformation. Protoplasts are transformed with plasmid DNA according to the small-scale transformation method of Hopwood et al. (Hopwood et al., *Genetic Manipulation of Streptomyces. A Laboratory Manual*, John Innes Foundation, Norwich, UK, 1985), Stutzman-Engwall and Hutchinson [Proc. Natl. Acad. Sci. USA 86:3135 (1988)] or Otten et al. [J. Bacteriol. 172:3427 (1990)]. After 17 hr of regeneration on R2YE medium at 30° C., the plates are overlayed with 25 to 50 microgram/ml of thiostrepton and allowed to grow at 30° C. until sporulated.

Conversion of ε-rhodomycinone to Daunorubicin by Fermentation

S. peucetius dnr-ORF6 transformants harboring a plasmid of the invention (pWHM954) are inoculated into liquid R2YE medium containing 10 microgram/ml of thiostrepton. After 2 days of growth at 27°–30° C., 2.5–3.5 ml of this culture is transferred to 25–35 ml of the GPS production medium [M. L. Dekleva, J. A. Titus, and W. R. Strohl. Can. J. Microbiol. 31:287(1985)] containing 10 µg/ml of thiostrepton and incubated at 27°–30° C. for 3–5 days on a rotary shaker at 250–280 rpm. The cultures are incubated in a water bath at 55° C. for 60 min after the addition of 25 milligram/ml of oxalic acid to hydrolyze the glycosidic forms of the anthracycline metabolites. The metabolites are extracted from the cultures with the same volume of acetonitrile:methanol (1:1, vol:vol) at 30° C. for 30–50 min on a rotary shaker at 280 rpm. The extract is filtered and the filtrate is analyzed by reversed-phase high pressure liquid chromatography (RP-HPLC). RP-HPLC is performed by using a Vydac $C_{18}$ column (4.6×250 mm; 5 micrometers particle size) at a flow rate of 0.385 ml/min. Mobile phase A is 0.1% trifluoroacetic acid (TFA, from Pierce Chemical Co.) in $H_2O$ and mobile phase B is 0.078% TFA in acetonitrile (from J. T. Baker Chemical Co.). Elution is performed with a linear gradient from 20 to 60% phase B in phase A in 33 minutes and monitored with a diode array detector set at 488 nm (bandwidth 12 micrometers). Daunorubicin and doxorubicin (10 microgram/ml in methanol) are used as external standards to quantitate the amount of these metabolites isolated from the cultures.

EXAMPLE 1

Figure 3:
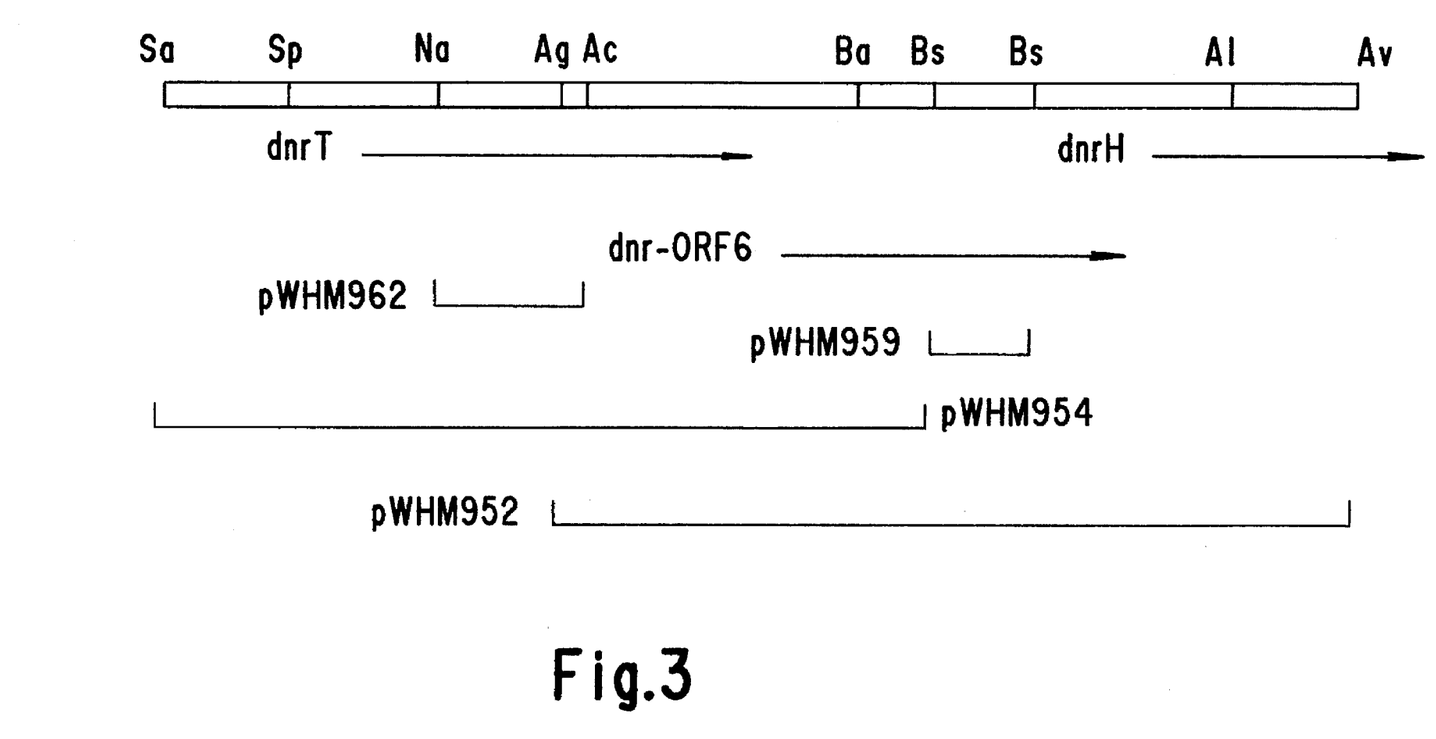

Disruption of dnr-ORF6 pWHM959 (FIG. 3) was constructed by subcloning a 411 bp BsaAI internal fragment (693 bp downstream of the hypothetical translational start site of dnr-ORF6) into a unique HincII site of pUC19, and transferring this construction as an EcoRI-HindIII fragment into plasmid pKC1139 (M. Bierman et al., Gene 116:43–49). The vector pKC139 contains a temperature-sensitive replicon that functions well at temperatures below 34° C. The 29050 strain was transformed with pWHM959, and transformants were selected with apramycin (25 µg/ml) at 30° C. Colonies from this transformation were grown in 5 ml liquid R2YE containing apramycin (10 µg/ml) at 30° C. for two days, then transferred to 39° C. for 5–7 days, to eliminate the autonomous vector and to select transformants in which homologous recombination between the cloned DNA and the chromosome had occured. A 0.5 ml portion of these cultures was plated on ISP4 plates containing apramycin (25 µg/ml) to verify integration of the plasmid. One of the resulting colonies, with the apramycin-resistant phenotype was examined by Southern analysis to verify the disruption of the dnr-ORF6 gene. The chromosomal DNA was digested with BamHI and probed with the pWHM959 DNA. The probe hybridized to 7.2 kb and 1.7 kb fragments for the dnr-ORF6 mutant strain, which is consistent with the insertion of the plasmid pKC1139 into the dnr-ORF6 gene. The wild-type strain showed the expected 2.0 kb BamHI dnr-ORF6 fragment.

EXAMPLE 2

Disruption of dnrT pWHM962 (FIG. 3) was constructed by subcloning a 555 bp AccI-NarI internal fragment (227 bp downstream of the hypothetical translational start site of dnrT) into a unique AccI site of pUC19, and transferring this construction as an EcoRI-HindIII fragment into pKC1139. The 29050 strain was transformed with pWHM962, and after selecting for apramycin resistance, the transformants were grown under apramycin selection at 39° C. to cause loss of the non-integrated plasmid. DNA from one of the resulting apramycin resistant colonies was analyzed by Southern blot-hybridization to affirm disruption of the dart gene. BamHI digested chromosomal DNA was probed with the 555 bp AccI-NarI fragment used for the inactivation and found to hybridize to 8.2 kb and 4.9 kb fragments for the dart mutant strain. This is consistent with the insertion of the plasmid pKC1139 into the dnrT gene since the wild-type strain showed the expected 6.0 kb BamHI dart fragment.

EXAMPLE 3

Cloning of the dnrT Gene Encoding an Enzyme Required for the Conversion of E-Rhodomycinone to Daunorubicin Several of the cosmid clones described by Stutzman-Engwall and Hutchinson [Proc. Natl. Acad. Sci. USA 86:3135 (1988)] and Otten et al. [J. Bacteriol. 172:3427 (1990)], such as pWHM335 or pWHM337, or similar clones obtained from equivalent strains, representing from approximately 20 up to 90 kb of S. peucetius 29050 genomic DNA, are digested with BamHI+SphI, the DNAs were combined with the pWHM3 vector or an equivalent vector that is capable of replication in both E. coli and Streptomyces spp. that has been digested with BamHI+SphI and religated, and the resulting mixture of plasmids is used to transform E. coli DH5α to ampicillin resistance (or to the resistance appropriate for selection of the vector used). The plasmid DNAs from several ampicillin resistance E. coli clones were introduced into the S. peucetius dnrT mutant, and the transformants were analysed for the bioconversion of ε-rhodomycinone to daunorubicin according to the method described in the Materials and Methods section. Plasmids with inserts encompassing the region of the restriction map shown in FIG. 1 were isolated and the desired insert subcloned as a 2.97 kb SacI-BsaAI DNA fragment into the SacI and HincII sites of the polylinker region of pUC19, then moving the gene as an EcoRI-HindIII segment into the polylinker region of pWHM3 to obtain pWHM954. S. peucetius dnrT(pWHM954) transformants were prepared as described in the Materials and Methods section and these were tested for the ability to bioconvert ε-rhodomycinone to daunorubicin.

EXAMPLE 4

Preparation of the S. peucetius dnr-ORF6 (pWHM954) Transformant Strain pWHM954 DNA was introduced in the S. peucetius dnr-ORF6 mutant by the protoplast-mediated transformation method described above, using thiostrepton (10 µg/ml) for selection of the recombinant strain. S. peucetius dnr-ORF6 (pWHM954) transformants were verified by re-isolation of pWHM954 according to the plasmid isolation protocol described in Hopwood et al. (Genetic manipulation of Streptomyces. A laboratory manual, John Innes Foundation, Norwich, UK, 1985) and the pWHM954 DNA analyzed by restriction enzyme digestion according to the standard methods described by Sambrook et al. (Molecular Cloning. A laboratory manual, 2nd ed., Cold Spring Harbor, N.Y., 1989).

EXAMPLE 5

Enhanced Conversion of ε-rhodomycinone (RHO) to Daunorubicin by S. peucetius dnr-ORF6 Transformants Harboring the pWHM954 Plasmid Carrying the dnrT Gene The S. peucetius dnr-ORF6 mutant carrying pWHM954 was grown for 12 days at 28° C. on slants of R2YE agar medium containing 50 µg/ml of thiostrepton. The spores of this culture are collected and suspended in 300 ml Erlenmeyer flasks containing 30 ml of R2YE liquid medium containing 10 µg/ml of thiostrepton and the flasks were shaken for 2 days at 30° C. on a rotary shaker running at 280 rpm in a 5 cm diameter cicle. Three ml of this culture were used to inoculate 30 ml of the GPS medium containing 10 µg/ml of thiostepton in 300 ml Erlenmeyer flasks. The flasks were incubated at 30° C. for 5 days under the same conditions described for the seed cultures, then placed in a water bath at 55° C. for 60 min after the addition of 25 mg/ml of solid oxalic acid to hydrolyze the glycosidic forms of the anthracycline metabolites. The metabolites were extracted from the cultures with 30 ml of acetonitrile:methanol (1:1 vol/vol) at 30° C. for 30 minutes on a rotary shaker at 280 rpm.

The extract was filtered and the filtrate analyzed by reverse-phase high pressure liquid chromatography (RP-HPLC). RP-HPLC was performed by using Vydac $C_{18}$ column.(4.6+250 mm; 5 µm particle size) at a flow rate of 0.385 ml/min. Mobile phase A is 0.1% trifluoroacetic acid (TFA from Pierce Chemical Co.) in $H_2O$ and mobile phase B is 0.078% TFA a acetonitrile (from J. T. Baker Chemical Co.) Elution was performed with a linear gradient from 20 to 60% phase B in phase A in 33 minutes and monitored with a diode array detector set 488 nm(bandwidth 12 µm). Daunorubicin (DNR)and doxorubicin (DXR) (10 µg/ml in methanol) were used as external standards to quantitate the amount of these methabolites isolated from the culture (Table 1).

TABLE 1

| RHO, DNR concentration ratio in extracts of cultures of S. peucetius dnr-ORF6 mutant transformed with pWHM954 containing the dnrT gene | | | | |
|---|---|---|---|---|
| Strain | RHO | DNR | DXR | RHO/DNR ratio |
| ATCC 29050 | 77 | 1 | ND[b] | 77 |
| dnr-ORF6 | 14.5 | 3.6 | 0.7 | 4 |
| dnr-ORF6/pWHM954 | 0.4 | 9.4 | 0.5 | 0.05 |

[a]µg/ml
[b]not determined

We claim:

1. An isolated DNA molecule encoding an ε-rhodomycinone conversion protein having a sequence at least 90% homologous to the sequence of SEQ ID NO. 2.

2. The DNA molecule according to claim 1, wherein the ε-rhodomycinone conversion protein has the sequence of SEQ ID NO. 2.

3. The DNA molecule according to claim 1, consisting of the sequence of SEQ ID NO. 1.

4. The vector encoding the ε-rhodomycinone conversion protein according to claim 1.

5. The vector according to claim 4 encoding an ε-rhodomycinone conversion protein having the sequence of SEQ ID NO:2.

6. The vector according to claim 4 encoding an ε-rhodomycinone conversion protein having a sequence at least 75% identical to the sequence of SEQ ID NO: 2.

7. The vector according to claim 4 comprising the sequence of SEQ ID NO:1.

8. The vector according to claim 4 which is a plasmid.

9. The plasmid according to claim 8 which is pWHM954.

10. A bacterial host transformed or transfected with the vector as claimed in claim 4.

11. The host according to claim 10 which is a Streptomyces cell.

12. The host according to claim 11 which is a Streptomyces cell having a mutation blocking the function of a gene of daunorubicin biosynthesis.

13. The host according to claim 12 wherein the gene is dnr-ORF6.

14. A process for producing daunorubicin, which process comprises:

(i) culturing a host according to claim 12 having the vector of claim 4, and (ii) isolating the daunorubicin from the culture.

15. A process for producing daunorubicin, which process comprises:

(i) culturing a host according to claim 13 having the plasmid of claim 9, and ii isolating the daunorubicin from the culture.

16. A process for producing the isolated DNA molecule according to claim 1, which process comprises:

(a) preparing a library of the genomic DNA of S. peucetius 29050 or a strain derived therefrom;

(b) screening the library for clones with the ability to convert ε-rhodomycinone to daunorubicin in a S. peucetius dnrT blocked mutant; and (c) obtaining an Insert DNA from a recombinant vector that forms part of the library and that has been screened as positive for the ability to convert ε-rhodomycinone to daunorubicin in the S. peucetius dnrT blocked mutant.

17. A Streptomyces cell having a mutation blocking the function of the gene dnr-ORF6.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 1518 base pairs
        ( B ) TYPE: nucleic acid
        ( C ) STRANDEDNESS: double
        ( D ) TOPOLOGY: linear     ( i i ) MOLECULE TYPE: cDNA     ( x i ) SEQUENCE DESCRIPTION: SEQ ID NO: 1:

```
ATGACCGCCC AGATCGCCCG GTCCGTCCTC GCCCGGGACG GCCTGGGCAG CGGCATGGAC    60
CGTTTCTGGG CGTGGTACGC CGACCGCTCG GCGCAGGTCG TGCACCGCAC CGAGCGGATT   120
CCGCTGGACG ACCTCAAGGG GTGGAGCCGC CACCCGGTCA CTGGGACCGT CTCCCATCAC   180
ACCGGGAGGT TCTTCAGCAT CGAGGGACTG GACGTGCACA TCCCGGGCGC CCCCGTGCCA   240
CGCTGGTCCC AGCCGATCGT GAACCAGCCC GAGGTGGGCA TCCTCGGCTT CCTGGTGAAG   300
GAGCGCCACG GGGTCCTGCA CTGCCTCGTC CAGGCCAAGT TCGAGCCGGG CAACCCCGGC   360
GGGCTTCAGC TCTCCCCTAC GGTCCAGGCC ACCCGCAGCA ACTACACGCG GTGCACGGC    420
GGCAAGGCCA TCCCGTACCT GGAGCACTTC CGCGACACCG CCGAACGGCA GGTGGTCGCC   480
GATGTGCTCC AGTCCGAACA GGGCTCCTGG TTCTACCGCA AGCGCAACCG CAACATGATC   540
GTCCAAGTGA TCGACGAGGT CCCGCTGCAC GAGGACTTCC ACTGGCTGAC GCTGGGTCAG   600
CTGCACCGGC TGCTGGGGGT CGAGAACCTC GTGAACATGG ACGCCAGGAC GGTGCTGGCC   660
TGCCTGCCGT TCGCGAGTGA GGGAGCGCAC CCGCTGGCCG ACGCGGAGCC GGCCGGAGCC   720
GACGGCCCCG GAGGTGGCCA CCCGGTGGTC CCCGCTCGAC CCGACGGCGG CGAGGGCCGG   780
GTAGACACCG GTTTCCACCG CTCCCTCGTG CGGTCGTGCG CGGCGGCCGA GGGCAGCCTG   840
CACAGCACCG TGGACATCGT CAGCTGGATC GCCGACCTGC GCAGCCGTAC CGACGTGGTC   900
ACCCGCCCGG CTGCGCTGAA CGCGCTGCCG CACTGGTACG AGCGGGACGG CGCGATCGCC   960
CACGAGAGCG GGCGCTTCCT GGAGGTGATG GCCGTCGACG TGACGGCCGC CTCGCGGGAG  1020
GTGCCCGGCT GGAGCCAGCC GATGATCGAA CCCAAGGACC AAGGGGTCGC GGCTTTCCTG  1080
GTCCGACGGA TCGACGGGGT TCTCCACGTC CTGGCGCACG CGCGCGTGGA GCCCGGCTAC  1140
GTCGACGTGG TGGAGATCGC GCCCACCGTA CAGTGCACCC CCGGCAGTCT GCACGCCCTG  1200
CCCGCCGAGG CCAGGCCCCG CTTCCTCGAC GCCGTGCTGG AGGCTCCACC CGAGCGCGTG  1260
CGCTACGCGA CCGTCCTCGC GGAGGAGGGA GGGCGCTTCT ACCACGCGGT GAACACCTAC  1320
ATGATCGTCG AAGCCGACCA TGACATCCCG GACGGTGGCG AATACCGCTG GCTGACGCTC  1380
CACCAACTGG TCGGGCTGCT GCGTCACTCC CACTACGTCA ACGTCCAGGC CCGCACCCTG  1440
GTCGCCTGTC TGCACAGCCT GTCCGTGGGC TCGCCCGTAA CCCGCTCAGC CGTGCCGTCC  1500
GCCCCGCCCC GGAGGTGA                                               1518
```

( 2 ) INFORMATION FOR SEQ ID NO: 2:

( i ) SEQUENCE CHARACTERISTICS:
        ( A ) LENGTH: 505 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO: 2:

| Met | Thr | Ala | Gln | Ile | Ala | Arg | Ser | Val | Leu | Ala | Arg | Asp | Gly | Leu | Gly |
|---|---|---|---|---|---|---|---|---|---|---|---|---|---|---|---|
| 1 | | | | 5 | | | | | 10 | | | | | 15 | |

| Ser | Gly | Met | Asp | Arg | Phe | Trp | Ala | Trp | Tyr | Ala | Asp | Arg | Ser | Ala | Gln |
|---|---|---|---|---|---|---|---|---|---|---|---|---|---|---|---|
| | | | 20 | | | | 25 | | | | | 30 | | | |

| Val | Val | His | Arg | Thr | Glu | Arg | Ile | Pro | Leu | Asp | Asp | Leu | Lys | Gly | Trp |
|---|---|---|---|---|---|---|---|---|---|---|---|---|---|---|---|
| | | | 35 | | | | 40 | | | | 45 | | | | |

| Ser | Arg | His | Pro | Val | Thr | Gly | Thr | Val | Ser | His | His | Thr | Gly | Arg | Phe |
|---|---|---|---|---|---|---|---|---|---|---|---|---|---|---|---|
| | 50 | | | | | 55 | | | | | 60 | | | | |

| Phe | Ser | Ile | Glu | Gly | Leu | Asp | Val | His | Ile | Pro | Gly | Ala | Pro | Val | Pro |
|---|---|---|---|---|---|---|---|---|---|---|---|---|---|---|---|
| 65 | | | | | 70 | | | | 75 | | | | | | 80 |

| Arg | Trp | Ser | Gln | Pro | Ile | Val | Asn | Gln | Pro | Glu | Val | Gly | Ile | Leu | Gly |
|---|---|---|---|---|---|---|---|---|---|---|---|---|---|---|---|
| | | | | 85 | | | | | 90 | | | | | 95 | |

| Phe | Leu | Val | Lys | Glu | Arg | His | Gly | Val | Leu | His | Cys | Leu | Val | Gln | Ala |
|---|---|---|---|---|---|---|---|---|---|---|---|---|---|---|---|
| | | | 100 | | | | | 105 | | | | 110 | | | |

| Lys | Phe | Glu | Pro | Gly | Asn | Pro | Gly | Gly | Leu | Gln | Leu | Ser | Pro | Thr | Val |
|---|---|---|---|---|---|---|---|---|---|---|---|---|---|---|---|
| | | 115 | | | | | 120 | | | | | 125 | | | |

| Gln | Ala | Thr | Arg | Ser | Asn | Tyr | Thr | Arg | Val | His | Gly | Gly | Lys | Ala | Ile |
|---|---|---|---|---|---|---|---|---|---|---|---|---|---|---|---|
| | 130 | | | | | 135 | | | | | 140 | | | | |

| Pro | Tyr | Leu | Glu | His | Phe | Arg | Asp | Thr | Ala | Glu | Arg | Gln | Val | Val | Ala |
|---|---|---|---|---|---|---|---|---|---|---|---|---|---|---|---|
| 145 | | | | | 150 | | | | 155 | | | | | | 160 |

| Asp | Val | Leu | Gln | Ser | Glu | Gln | Gly | Ser | Trp | Phe | Tyr | Arg | Lys | Arg | Asn |
|---|---|---|---|---|---|---|---|---|---|---|---|---|---|---|---|
| | | | | 165 | | | | | 170 | | | | | 175 | |

| Arg | Asn | Met | Ile | Val | Gln | Val | Ile | Asp | Glu | Val | Pro | Leu | His | Glu | Asp |
|---|---|---|---|---|---|---|---|---|---|---|---|---|---|---|---|
| | | | 180 | | | | | 185 | | | | 190 | | | |

| Phe | His | Trp | Leu | Thr | Leu | Gly | Gln | Leu | His | Arg | Leu | Leu | Gly | Val | Glu |
|---|---|---|---|---|---|---|---|---|---|---|---|---|---|---|---|
| | | 195 | | | | | 200 | | | | | 205 | | | |

| Asn | Leu | Val | Asn | Met | Asp | Ala | Arg | Thr | Val | Leu | Ala | Cys | Leu | Pro | Phe |
|---|---|---|---|---|---|---|---|---|---|---|---|---|---|---|---|
| | 210 | | | | | 215 | | | | | 220 | | | | |

| Ala | Ser | Glu | Gly | Ala | His | Pro | Leu | Ala | Asp | Ala | Glu | Pro | Ala | Gly | Ala |
|---|---|---|---|---|---|---|---|---|---|---|---|---|---|---|---|
| 225 | | | | | 230 | | | | 235 | | | | | | 240 |

| Asp | Gly | Pro | Gly | Gly | Gly | His | Pro | Val | Val | Pro | Ala | Arg | Pro | Asp | Gly |
|---|---|---|---|---|---|---|---|---|---|---|---|---|---|---|---|
| | | | | 245 | | | | | 250 | | | | | 255 | |

| Gly | Glu | Gly | Arg | Val | Asp | Thr | Gly | Phe | His | Arg | Ser | Leu | Val | Arg | Ser |
|---|---|---|---|---|---|---|---|---|---|---|---|---|---|---|---|
| | | | 260 | | | | | 265 | | | | 270 | | | |

| Cys | Ala | Ala | Ala | Glu | Gly | Ser | Leu | His | Ser | Thr | Val | Asp | Ile | Val | Ser |
|---|---|---|---|---|---|---|---|---|---|---|---|---|---|---|---|
| | | 275 | | | | | 280 | | | | | 285 | | | |

| Trp | Ile | Ala | Asp | Leu | Arg | Ser | Arg | Thr | Asp | Val | Val | Thr | Arg | Pro | Ala |
|---|---|---|---|---|---|---|---|---|---|---|---|---|---|---|---|
| | 290 | | | | | 295 | | | | | 300 | | | | |

| Ala | Leu | Asn | Ala | Leu | Pro | His | Trp | Tyr | Glu | Arg | Asp | Gly | Ala | Ile | Ala |
|---|---|---|---|---|---|---|---|---|---|---|---|---|---|---|---|
| 305 | | | | | 310 | | | | 315 | | | | | | 320 |

| His | Glu | Ser | Gly | Arg | Phe | Leu | Glu | Val | Met | Ala | Val | Asp | Val | Thr | Ala |
|---|---|---|---|---|---|---|---|---|---|---|---|---|---|---|---|
| | | | | 325 | | | | | 330 | | | | | 335 | |

| Ala | Ser | Arg | Glu | Val | Pro | Gly | Trp | Ser | Gln | Pro | Met | Ile | Glu | Pro | Lys |
|---|---|---|---|---|---|---|---|---|---|---|---|---|---|---|---|
| | | | 340 | | | | | 345 | | | | | 350 | | |

| Asp | Gln | Gly | Val | Ala | Ala | Phe | Leu | Val | Arg | Arg | Ile | Asp | Gly | Val | Leu |
|---|---|---|---|---|---|---|---|---|---|---|---|---|---|---|---|
| | | 355 | | | | | 360 | | | | | 365 | | | |

| His | Val | Leu | Ala | His | Ala | Arg | Val | Glu | Pro | Gly | Tyr | Val | Asp | Val | Val |
|---|---|---|---|---|---|---|---|---|---|---|---|---|---|---|---|
| | 370 | | | | | 375 | | | | | 380 | | | | |

| Glu | Ile | Ala | Pro | Thr | Val | Gln | Cys | Thr | Pro | Gly | Ser | Leu | His | Ala | Leu |
|---|---|---|---|---|---|---|---|---|---|---|---|---|---|---|---|
| 385 | | | | | 390 | | | | 395 | | | | | | 400 |

|   |   |   |   |   |   |   |   |   |   |   |   |   |   |   |
|---|---|---|---|---|---|---|---|---|---|---|---|---|---|---|
| Pro | Ala | Glu | Ala | Arg<br>405 | Pro | Arg | Phe | Leu | Asp<br>410 | Ala | Val | Leu | Glu | Ala Pro<br>415 |
| Pro | Glu | Arg | Val<br>420 | Arg | Tyr | Ala | Thr | Val<br>425 | Leu | Ala | Glu | Glu | Gly<br>430 | Gly Arg |
| Phe | Tyr | His<br>435 | Ala | Val | Asn | Thr | Tyr<br>440 | Met | Ile | Val | Glu | Ala<br>445 | Asp | His Asp |
| Ile | Pro<br>450 | Asp | Gly | Gly | Glu | Tyr<br>455 | Arg | Trp | Leu | Thr | Leu<br>460 | His | Gln | Leu Val |
| Gly<br>465 | Leu | Leu | Arg | His | Ser<br>470 | His | Tyr | Val | Asn | Val<br>475 | Gln | Ala | Arg | Thr Leu<br>480 |
| Val | Ala | Cys | Leu | His<br>485 | Ser | Leu | Ser | Val | Gly<br>490 | Ser | Pro | Val | Thr | Arg Ser<br>495 |
| Ala | Val | Pro | Ser<br>500 | Ala | Pro | Pro | Arg | Arg<br>505 | | | | | | |

( 2 ) INFORMATION FOR SEQ ID NO: 3:

( i ) SEQUENCE CHARACTERISTICS:
        ( A ) LENGTH: 1332 base pairs
        ( B ) TYPE: nucleic acid
        ( C ) STRANDEDNESS: double
        ( D ) TOPOLOGY: linear     ( i i ) MOLECULE TYPE: cDNA     ( x i ) SEQUENCE DESCRIPTION: SEQ ID NO: 3:

```
GTGCGCGTCC TGTTCGCCAC CATGGCCGCG CGGTCCCATG TCTACGCCCA GGTCACCCTG    60
GCGTCGGCAC TGCGGACCGC GGGGCACGAA GTGCTCGTGG CCAGCAGCC CGACGTCCTC    120
GACGACATCG TCCGGGCCGG TCTCACCGCC GTGCGGATCG GGAGGACCT CAACATCGAG    180
GAGGAGACCC GGGAGGCCAA CGCCAGCTTC GAGGACGACC GCAACCTCGG GGCCTCGCC    240
ATGAGCAACT CCCGTGATGA CCCCTTCCCG TGGGACCACG CGCTCGGCAT GTTCACCGCG    300
ATGACCGCCA TGGTCTTCCA GAACGTGTGC CCCGAGCCCA TGGTCGACGA CCTCGTCGGC    360
CTCGCCCGCG ACTGGCGGCC GGACCTCGTG GTCTGGGATC CGCTGACCCT GGCCGGGCCG    420
GTGGCCGCCC GGCTCAGCGG GGCGGCGCAC GCCCGGCTGC TGTTCGGCCC GGACCAGATG    480
GGCCGGAACA GGACGGCGTT CCGCGCCCTG CTCGACCGGC AACCGCCCGA GCTGCGCGAC    540
GACCCGCTGG CCGAGTGGCT CACCTGGACG CTGGAGCGGT GCGGCGGCAG CGCCGGGGAC    600
ATGAGCGAGG AGCTGGTCCT CGGGCAGTGG ACGATCGACC CCACACCGCC GTCGATGCGC    660
ATCCCCCTGG ACCTGCCCTG CGTGCCGGTG CGCTACGTGC CGTACAACGG GCCCTCCCTG    720
CTCCCCGGCT GGCTGCGCGA GCCGCCCCGC CACCCGCGGC GCCTGTGCCT GACGCTCGGT    780
GTGTCCCTCG GCGAGGCGAC GGGCGCCGGC ACGGTCGCCG CCTCCGACGT CCTGGCGGCC    840
GTGGACGGCC TGGACGTGGA GGTCGTCGCC ACCCTGCCGC GGGAACTGCG CGAGGAGCTC    900
GGCACCCTGC CGGCGAACGT GCGGGCCGTG GACTTCGTCC CGCTGAACGC CCTGCTGCCG    960
TCCTGCTCGG GCATCATCCA TCACGGCGGG TCCGGCACGT TCATGACGGC CCTGGTGCAC    1020
GCGATACCGC AGCTGATCGT GCCTGACATG ATGTGGGACG CCATGGAGAA GGCACACGGC    1080
CTGGCCCGCA GCGGTGCGGG CAGTTACGTG GACGCGCGGG ACGTCTCGCC GGAACTGCTG    1140
CGCGAGCGCG TCCTCGCCCT GCTCGACGAT CCGTCCTACG CCGCCGGGGC ACGCCGGGTG    1200
CGCGCCGAGA TCGTCGGGAC GCCGAGCCCG AACGACATCG TGCCCGTGCT GGAGCGGCTG    1260
ACCGCCGAGC ACCGGGCCGG CGGGGCGGAG GGGGGCCCGG CGCTCAAGTC GCCTTCCACC    1320
GGCGGTGCCT AG                                                       1332
```

( 2 ) INFORMATION FOR SEQ ID NO: 4:

( i ) SEQUENCE CHARACTERISTICS:
        ( A ) LENGTH: 443 amino acids
        ( B ) TYPE: amino acid
        ( C ) STRANDEDNESS:
        ( D ) TOPOLOGY: linear     ( i i ) MOLECULE TYPE: protein     ( x i ) SEQUENCE DESCRIPTION: SEQ ID NO: 4:

```
Met Arg Val Leu Phe Ala Thr Met Ala Ala Arg Ser His Val Tyr Ala
 1               5                  10                  15

Gln Val Thr Leu Ala Ser Ala Leu Arg Thr Ala Gly His Glu Val Leu
                20                  25                  30

Val Ala Ser Gln Pro Asp Val Leu Asp Asp Ile Val Arg Ala Gly Leu
            35                  40                  45

Thr Ala Val Arg Ile Gly Glu Asp Leu Asn Ile Glu Glu Thr Arg
 50                      55                  60

Glu Ala Asn Ala Ser Phe Glu Asp Asp Arg Asn Leu Gly Gly Leu Ala
 65                  70                  75                  80

Met Ser Asn Ser Arg Asp Asp Pro Phe Pro Trp Asp His Ala Leu Gly
                85                  90                  95

Met Phe Thr Ala Met Thr Ala Met Val Phe Gln Asn Val Cys Pro Glu
            100                 105                 110

Pro Met Val Asp Asp Leu Val Gly Leu Ala Arg Asp Trp Arg Pro Asp
        115                 120                 125

Leu Val Val Trp Asp Pro Thr Leu Ala Gly Pro Val Ala Ala Arg
    130                 135                 140

Leu Ser Gly Ala Ala His Ala Arg Leu Leu Phe Gly Pro Asp Gln Met
145                 150                 155                 160

Gly Arg Asn Arg Thr Ala Phe Arg Ala Leu Leu Asp Arg Gln Pro Pro
                165                 170                 175

Glu Leu Arg Asp Asp Pro Leu Ala Glu Trp Leu Thr Trp Thr Leu Glu
            180                 185                 190

Arg Cys Gly Gly Ser Ala Gly Asp Met Ser Glu Glu Leu Val Leu Gly
        195                 200                 205

Gln Trp Thr Ile Asp Pro Thr Pro Pro Ser Met Arg Ile Pro Leu Asp
    210                 215                 220

Leu Pro Cys Val Pro Val Arg Tyr Val Pro Tyr Asn Gly Pro Ser Leu
225                 230                 235                 240

Leu Pro Gly Trp Leu Arg Glu Pro Pro Arg His Pro Arg Arg Leu Cys
                245                 250                 255

Leu Thr Leu Gly Val Ser Leu Gly Glu Ala Thr Gly Ala Gly Thr Val
            260                 265                 270

Ala Ala Ser Asp Val Leu Ala Ala Val Asp Gly Leu Asp Val Glu Val
        275                 280                 285

Val Ala Thr Leu Pro Arg Glu Leu Arg Glu Glu Leu Gly Thr Leu Pro
    290                 295                 300

Ala Asn Val Arg Ala Val Asp Phe Val Pro Leu Asn Ala Leu Leu Pro
305                 310                 315                 320

Ser Cys Ser Gly Ile Ile His His Gly Gly Ser Gly Thr Phe Met Thr
                325                 330                 335

Ala Leu Val His Ala Ile Pro Gln Leu Ile Val Pro Asp Met Met Trp
            340                 345                 350

Asp Ala Met Glu Lys Ala His Gly Leu Ala Arg Ser Gly Ala Gly Ser
```

|   | 355 |   |   |   |   | 360 |   |   |   |   | 365 |   |   |   |
|---|---|---|---|---|---|---|---|---|---|---|---|---|---|---|
| Tyr | Val 370 | Asp | Ala | Arg | Asp | Val 375 | Ser | Pro | Glu | Leu | Leu 380 | Arg | Glu | Arg | Val |
| Leu 385 | Ala | Leu | Leu | Asp | Asp 390 | Pro | Ser | Tyr | Ala | Ala 395 | Gly | Ala | Arg | Arg | Val 400 |
| Arg | Ala | Glu | Ile | Val 405 | Gly | Thr | Pro | Ser | Pro 410 | Asn | Asp | Ile | Val | Pro 415 | Val |
| Leu | Glu | Arg | Leu 420 | Thr | Ala | Glu | His | Arg 425 | Ala | Gly | Gly | Ala | Glu 430 | Gly | Gly |
| Pro | Ala | Leu 435 | Lys | Ser | Pro | Ser | Thr 440 | Gly | Gly | Ala |   |   |   |   |   |